US012345720B2

(12) United States Patent
Nouso et al.

(10) Patent No.: US 12,345,720 B2
(45) Date of Patent: Jul. 1, 2025

(54) METHOD FOR AIDING DETECTION OF NONALCOHOLIC STEATOHEPATITIS

(71) Applicants: Denka Company Limited, Tokyo (JP); NATIONAL UNIVERSITY CORPORATION HOKKAIDO UNIVERSITY, Sapporo (JP); Kazuhiro Nouso, Okayama (JP)

(72) Inventors: Kazuhiro Nouso, Okayama (JP); Yasuki Ito, Gosen (JP); Motoko Ohta, Gosen (JP); Hitoshi Chiba, Sapporo (JP); Toshihiro Sakurai, Sapporo (JP); Hiroyuki Okada, Okayama (JP)

(73) Assignees: DENKA COMPANY LIMITED, Tokyo (JP); NATIONAL UNIVERSITY CORPORATION HOKKAIDO UNIVERSITY, Sapporo (JP); KAZUHIRO NOUSO, Okayama (JP)

( * ) Notice: Subject to any disclaimer, the term of this patent is extended or adjusted under 35 U.S.C. 154(b) by 951 days.

(21) Appl. No.: 17/270,190

(22) PCT Filed: Aug. 22, 2019

(86) PCT No.: PCT/JP2019/032738
§ 371 (c)(1),
(2) Date: Feb. 22, 2021

(87) PCT Pub. No.: WO2020/040238
PCT Pub. Date: Feb. 27, 2020

(65) Prior Publication Data
US 2021/0199676 A1   Jul. 1, 2021

(30) Foreign Application Priority Data

Aug. 23, 2018   (JP) .................................. 2018-156797

(51) Int. Cl.
*G01N 33/92*   (2006.01)
(52) U.S. Cl.
CPC ....... *G01N 33/92* (2013.01); *G01N 2800/085* (2013.01); *G01N 2800/56* (2013.01)
(58) Field of Classification Search
None
See application file for complete search history.

(56) References Cited

U.S. PATENT DOCUMENTS

| | | | | |
|---|---|---|---|---|
| 2006/0195308 A1* | 8/2006 | Kadambi | ................. | A61P 3/06 703/11 |
| 2009/0226944 A1* | 9/2009 | Katayama | ................. | C12Q 1/61 435/11 |
| 2017/0370954 A1 | 12/2017 | Perichon et al. | | |

FOREIGN PATENT DOCUMENTS

| | | |
|---|---|---|
| JP | 2010-94131 A | 4/2010 |
| JP | 2014-30393 A | 2/2014 |
| JP | 2018-502286 A | 1/2018 |
| JP | 2018-80943 A | 5/2018 |
| JP | 2018-124219 A | 8/2018 |
| WO | WO 2016/081534 A1 | 5/2016 |

OTHER PUBLICATIONS

Yasuki JP 2014030393 English Translation (Year: 2014).*
Qi (Journal of Lipidology 2018 12:89-98). (Year: 2018).*
Hiroe (Diabetes 2018 Supp. 1, p. A163 Abstract; 78th Scientific Sessions of the American Diabetes Association, Orlando FL (Year: 2018).*
Musso Hepatology 2003 37:909-916 (Year: 2003).*
Lambert Gastroenterology 2014 146:726-735 (Year: 2014).*
Ito JALM Mar. 2018 746-756 (Year: 2018).*
Extended European Search Report for European Application No. 19851821.9, dated Apr. 11, 2022.
Männistö et al., "Lipoprotein subclass metabolism in nonalcoholic steatohepatitis", Journal of Lipid Research, vol. 55, Dec. 1, 2014, pp. 2676-2684.
Shinohata et al., "Low plasma apolipoprotein E-rich high-density lipoprotein levels in patients with metabolic syndrome", Clinica Chimica Acta, Elsevier BV, Amsterdam, NL, vol. 510, Aug. 14, 2020, pp. 531-536.
Fujita et al., "Dysfunctional Very-Low-Density Lipoprotein Synthesis and Release Is a Key Factor in Nonalcoholic Steatohepatitis Pathogenesis," Hepatology, vol. 50, No. 3, 2009, pp. 772-780, 9 pages total.
Ikeda et al., "A rapid and precise method for measuring plasma apoE-rich HDL using polyethylene glycol and cation-exchange chromatography: a pilot study on the clinical significance of apoE-rich HDL measurements," Clinica Chimica Acta, vol. 465, 2017, pp. 112-118, 7 pages total.

* cited by examiner

*Primary Examiner* — Changhwa J Cheu
(74) *Attorney, Agent, or Firm* — Birch, Stewart, Kolasch & Birch, LLP

(57) ABSTRACT

Provided are a method of assisting the detection of nonalcoholic steatohepatitis (NASH) and a method that is able to assist in determining the degree of progression of any condition associated with NASH, which are far less invasive than liver biopsy and include simple operations and are independent of the skills of technicians.
The present invention provides a method of assisting the detection of nonalcoholic steatohepatitis, including measuring the abundance of LDL-TG and/or ApoE-rich HDL-C contained in a test blood sample isolated from a living body. Also, the present invention provides a method of assisting in determining the degree of progression of at least one medical condition associated with nonalcoholic steatohepatitis, which medical condition(s) is(are) selected from the group consisting of fatty degeneration (steatosis), inflammation, ballooning degeneration, and fibrosis, including measuring the abundance of LDL-TG and/or ApoE-rich HDL-C contained in a test blood sample isolated from a living body.

10 Claims, 9 Drawing Sheets

METHOD FOR AIDING DETECTION OF NONALCOHOLIC STEATOHEPATITIS

TECHNICAL FIELD

The present invention relates to a method of assisting the detection of nonalcoholic steatohepatitis and to a method of assisting in determining the degree of progression of any condition associated with nonalcoholic steatohepatitis.

BACKGROUND ART

Nonalcoholic fatty liver disease (hereinafter also referred to as "NAFLD") refers to a group of medical conditions characterized by steatosis, which is confirmed by histological examination or diagnostic imaging, except for liver diseases such as viral hepatitis, autoimmune hepatitis, and alcoholic liver disease. The prevalence of this disease is rapidly increasing worldwide in association with an increasing number of people who suffer from obesity. Nonalcoholic fatty liver disease (NAFLD) is classified into nonalcoholic fatty liver (hereinafter also referred to as "NAFL"), which is thought to rarely progress, and nonalcoholic steatohepatitis (hereinafter also referred to as "NASH"), which is progressive and causes liver cirrhosis and liver cancer. The pathological characteristics of nonalcoholic steatohepatitis (NASH) include, for example, fatty degeneration (steatosis), ballooning degeneration, inflammation, and fibrosis.

A definitive diagnosis based on liver biopsy is required to identify various disease states in the liver, including fatty degeneration (steatosis), and to distinguish between NAFL and NASH. However, liver biopsy is an invasive and expensive examination, and therefore causes patients to feel exhausted in different ways. Additionally, the skills of practicing technicians may affect the accuracy of liver biopsy, as exemplified by sampling errors that occur at a certain probability, and the same is true for examination of collected samples. Thus, patients need to visit specific institutions to receive a certain level of therapy, which has, problematically, increased burden on patients.

Meanwhile, examples of laboratory test items that are commonly analyzed in relation to diagnosis of liver diseases include AST, ALT, AST/ALT ratio, and the like; markers for inflammation and cytokine secretion, such as TNF-α, high-sensitivity CRP, and ferritin; cytokeratin 18 fragments as apoptosis markers; and fibrosis markers, such as hyaluronic acid and type IV collagen 7S (Patent Documents 1 and 2). However, there have not been established biomarkers for predicting the presence of NASH, which are detected in people who suffer from any medical condition associated with NASH. That is, there has not been found any biomarkers that comprehensively reflect the pathological characteristics associated with NASH.

PRIOR ART DOCUMENTS

Patent Documents

Patent Document 1: JP 2010-94131 A
Patent Document 2: JP 2018-80943 A

SUMMARY OF THE INVENTION

Problems to be Solved by the Invention

An object of the present invention is to provide a method of assisting the detection of nonalcoholic steatohepatitis (NASH) and a method that is able to assist in determining the degree of progression of any condition associated with NASH, which are far less invasive than liver biopsy and include simple operations and are independent of the skills of technicians.

Means for Solving the Problem

The inventors studied hard, and consequently found that measurement of the abundance of LDL-TG and/or ApoE-rich HDL-C contained in a test blood sample isolated from a living body, which includes simple operations, can assist the detection of NASH, and can also assist in determining the degree of progression of any condition associated with NASH, without liver biopsy, and finally completed the present invention.

That is, the present invention is as follows.

[1] A method of assisting the detection of nonalcoholic steatohepatitis, comprising measuring the abundance of LDL-TG and/or ApoE-rich HDL-C contained in a test blood sample isolated from a living body.

[2] The method according to [1], wherein the method uses as an index the abundance of LDL-TG in the test blood sample, and a higher abundance of LDL-TG in the test blood sample than that in blood samples from patients with nonalcoholic fatty liver indicates a greater possibility of having nonalcoholic steatohepatitis.

[3] The method according to [1] or [2], wherein the method uses as an index the LDL-TG/LDL-C ratio in the test blood sample, and a higher LDL-TG/LDL-C ratio in the test blood sample than that in blood samples from patients with nonalcoholic fatty liver indicates a greater possibility of having nonalcoholic steatohepatitis.

[4] The method according to any one of [1] to [3], wherein the method uses as an index the ApoE-rich HDL-C/HDL-C ratio in the test blood sample, and a lower ApoE-rich HDL-C/HDL-C ratio in the test blood sample than that in blood samples from patients with alcoholic fatty liver indicates a greater possibility of having nonalcoholic steatohepatitis.

[5] A method of assisting in determining the degree of progression of at least one medical condition associated with nonalcoholic steatohepatitis, which medical condition(s) is(are) selected from the group consisting of fatty degeneration (steatosis), inflammation, ballooning degeneration, and fibrosis, comprising measuring the abundance of LDL-TG and/or ApoE-rich HDL-C contained in a test blood sample isolated from a living body.

Effect of the Invention

The present invention can assist in detecting NASH or in determining the degree of progression of and/or presence or absence of any condition associated with NASH, through safe and simple operations and also independently of the skills of technicians who practice liver biopsy, while liver biopsy, which increases burden and risk on patients, is avoided as much as possible. Consequently, patients can start treatment earlier in the course of NASH, and recognize the risk of disease progression so that the patients can be assisted in determining a treatment plan, which can prevent or delay disease progression to sever stages or death.

MODE FOR CARRYING OUT THE INVENTION

The present invention relates to methods of assisting the detection of nonalcoholic steatohepatitis (NASH) and of assisting in determining the degree of progression of any condition associated with nonalcoholic steatohepatitis (NASH), by measuring the abundance of LDL-TG and/or ApoE-rich HDL-C contained in a test blood sample isolated from a living body.

In the present invention, LDL-TG refers to triglycerides (TG) in low-density lipoproteins (hereinafter referred to as LDL), and ApoE-rich HDL-C refers to cholesterol (C) in apolipoprotein E-rich high-density lipoproteins (hereinafter referred to as ApoE-rich HDL).

The present invention uses blood samples as test samples and is thus far less invasive than liver biopsy, and can contribute to comprehensive understanding of the medical condition of the entire liver, independently of a specific sample obtained by resecting a portion of the liver. Additionally, test blood samples are easily collected, and the abundance of LDL-TG and/or ApoE-rich HDL-C contained in the blood samples can be measured with a simple operation as easy as, for example, routine medical practice or physical examination when an assay kit compatible with automated analyzers is used. Blood samples in the present invention include whole blood, plasma, and serum samples.

(Method of Assisting the Detection of Nonalcoholic Steatohepatitis (NASH))

The method of the present invention for assisting the detection of nonalcoholic steatohepatitis (NASH) is specifically described below.

(1) Abundance of LDL-TG

Figure 4:
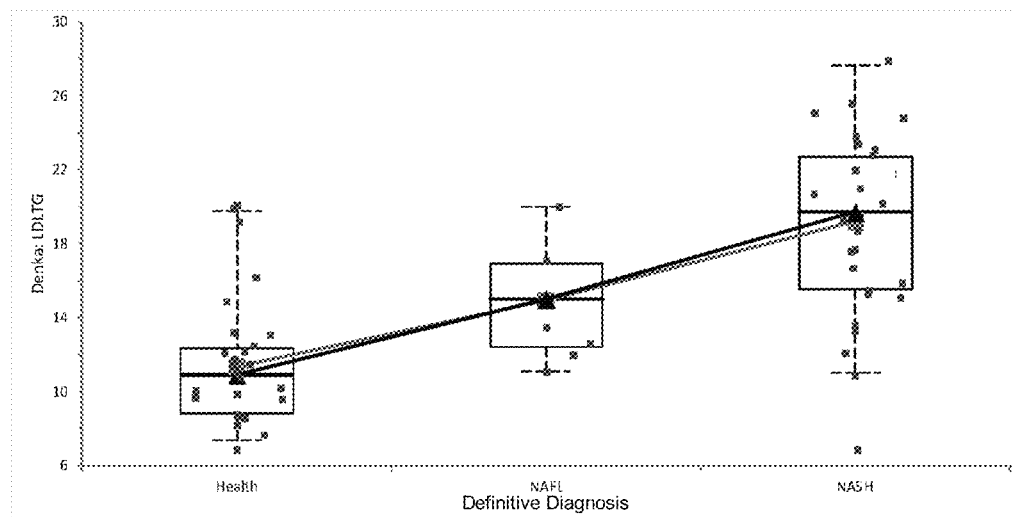
FIG. 4 shows the result of measuring the LDL-TG content in blood samples collected from test subjects in Example 1.

The abundance of LDL-TG (also referred to as LDL-TG content) in a test blood sample is measured as an index. If the test blood sample shows a significantly higher LDL-TG content than that in blood samples from nonalcoholic fatty liver (NAFL) patients (NAFL patients), the LDL-TG content in the test blood sample can be recognized as indicating a greater possibility of having NASH (see Example 1, Example 4, and FIG. 4). The analysis of the LDL-TG content in a blood sample identifies a nonalcoholic steatohepatitis patient (NASH patient) with a sensitivity of 82.9% and a specificity of 55.6% when the cut-off value is set at 15.1 mg/dL, and with a sensitivity of 65.7% and a specificity of 88.9% when the cut-off value is set at 17.6 mg/dL, and with a sensitivity of 94.3% and a specificity of 22.2% when the cut-off value is set at 12.1 mg/dL, and with a sensitivity of 48.6% and a specificity of 100% when the cut-off value is set at 20.2 mg/dL. In this respect, the cut-off value used to identify NASH patients can be set at an appropriate value within the range depending on the sensitivity and specificity determined by those who use this invention; for example, the cut-off value of the LDL-TG content is within the range of 12.1 to 21.2 mg/dL, and is preferably within the range of 17.6 mg/dL±20%, and is most preferably 17.6 mg/dL. The LDL-TG content in blood samples from NAFL patients can be determined by analyzing the blood samples previously collected from a population of NAFL patients.

(2) LDL-TG/LDL-C Ratio

Figure 5:
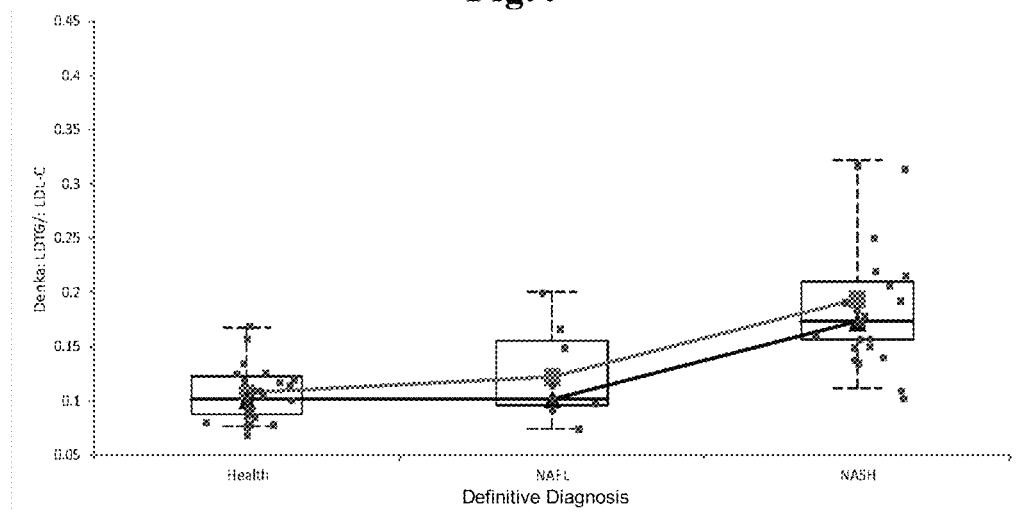
FIG. 5 shows the result of calculating the LDL-TG/LDL-C ratio in blood samples collected from test subjects in Example 2-1.

The LDL-TG content and the LDL-C content in a test blood sample are measured, and the LDL-TG/LDL-C ratio is calculated as an index. If the test blood sample shows a significantly higher LDL-TG/LDL-C ratio than that in blood samples from healthy individuals or NAFL patients, the LDL-TG/LDL-C ratio in the test blood sample can be recognized as indicating a greater possibility of having NASH (see Example 2-1, Example 5-1, and FIG. 5). As used herein, the LDL-C content refers to the abundance of cholesterol (C) in low-density lipoproteins (LDL). The analysis of the LDL-TG/LDL-C ratio in a blood sample identifies a NASH patient with a sensitivity of 100% and a specificity of 55.6% when the cut-off value is set at 0.103, and with a sensitivity of 94.3% and a specificity of 66.7% when the cut-off value is set at 0.133, and with a sensitivity of 82.9% and a specificity of 77.8% when the cut-off value is set at 0.149, and with a sensitivity of 31.4% and a specificity of 100% when the cut-off value is set at 0.203. In this respect, the cut-off value used to identify NASH patients can be set at an appropriate value within the range depending on the sensitivity and specificity determined by those who use this invention; for example, the cut-off value of the LDL-TG/LDL-C ratio is within the range of 0.103 to 0.203, and is preferably within the range of 0.133±20%, and is most preferably 0.149 or 0.133.

Figure 6:
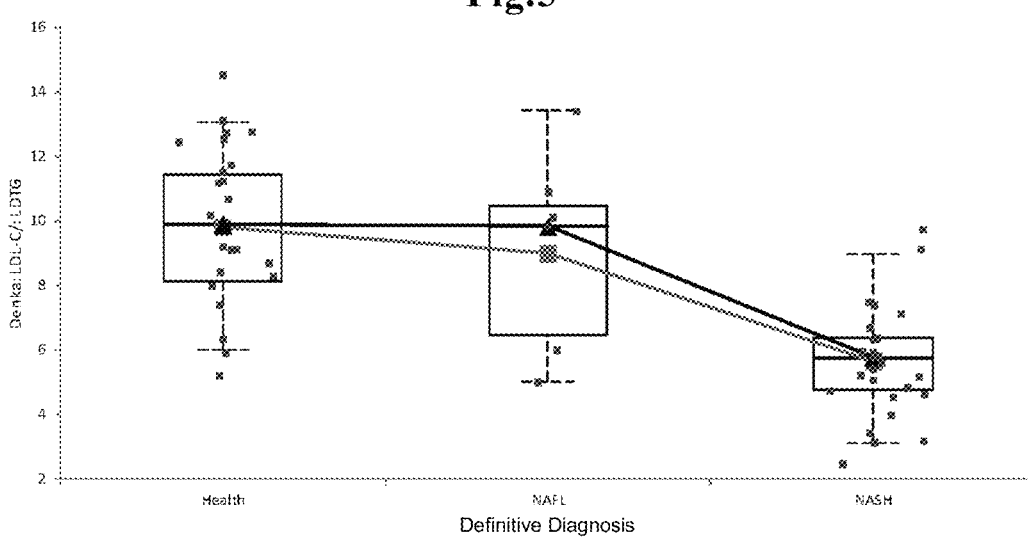
FIG. 6 shows the result of calculating the LDL-C/LDL-TG ratio in blood samples collected from test subjects in Example 2-2.

Furthermore, the LDL-C/LDL-TG ratio in the test blood sample is calculated as an index. If the LDL-C/LDL-TG ratio in the test blood sample is lower than that in blood samples from healthy individuals or NAFL patients, the LDL-C/LDL-TG ratio in the test blood sample can also be recognized as indicating a greater possibility of having NASH (see Example 2-2, Example 5-2, and FIG. 6). The analysis of the LDL-C/LDL-TG ratio in a blood sample identifies a NASH patient with a sensitivity of 100% and a specificity of 55.6% when the cut-off value is set at 9.75, and with a sensitivity of 94.3% and a specificity of 66.7% when the cut-off value is set at 7.50, and with a sensitivity of 82.9% and a specificity of 77.8% when the cut-off value is set at 6.70, and with a sensitivity of 31.4% and a specificity of 100% when the cut-off value is set at 4.93. In this case, the LDL-C/LDL-TG ratio is the inverse ratio of the LDL-TG/LDL-C ratio. In this respect, the cut-off value used to identify NASH patients can be set at an appropriate value within the range depending on the sensitivity and specificity determined by those who use this invention; for example, the cut-off value of the LDL-C/LDL-TG ratio is within the range of 4.93 to 9.75, and is preferably within the range of 7.50±20%, and is most preferably 7.50 or 6.70.

(3) ApoE-Rich HDL-C/HDL-C Ratio

Figure 8:
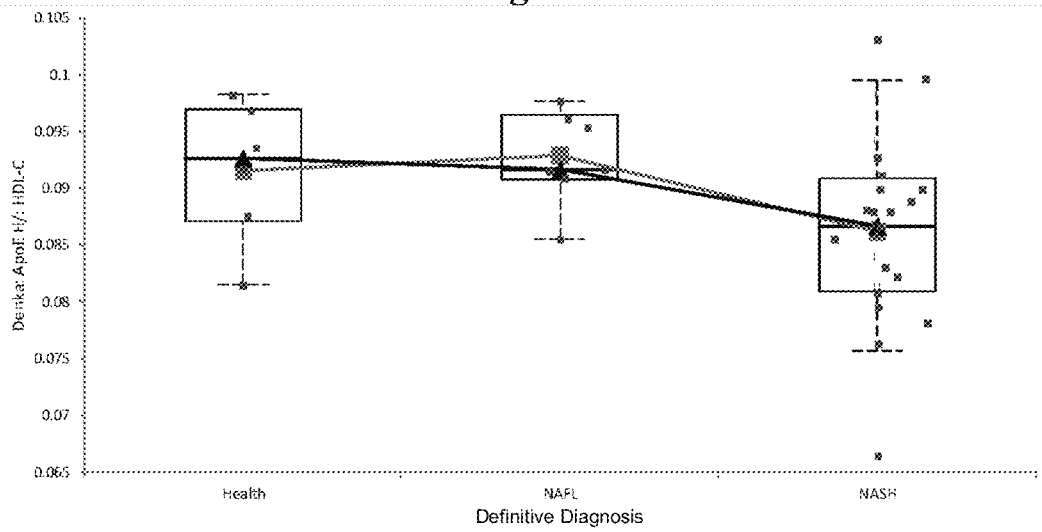
FIG. 8 shows the result of calculating the ApoE-rich HDL-C/HDL-C ratio in blood samples collected from test subjects in Example 3-1.

The ApoE-rich HDL-C content and the HDL-C content in a test blood sample are measured, and the ApoE-rich HDL-C/HDL-C ratio is calculated as an index. If the test blood sample shows a significantly lower ApoE-rich HDL-C/HDL-C ratio than that in blood samples from NAFL patients, the ApoE-rich HDL-C/HDL-C ratio in the test blood sample can be recognized as indicating a greater possibility of having NASH (see Example 3-1, Example 13-1, and FIG. 8). As used herein, the HDL-C content refers to the abundance of cholesterol (C) in high-density lipoproteins (HDL). The analysis of the ApoE-rich HDL-C/HDL-C ratio in a blood sample identifies a NASH patient with a sensitivity of 80.0% and a specificity of 66.7% when the cut-off value is set at 0.0912, and with a sensitivity of 74.3% and a specificity of 88.9% when the cut-off value is set at 0.0899, and with a sensitivity of 42.9% and a specificity of 100% when the cut-off value is set at 0.0840, and with a sensitivity of 91.4% and a specificity of 11.1% when the cut-off value is set at 0.0971. In this respect, the cut-off value used to identify NASH patients can be set at an appropriate value within the range depending on the sensitivity and specificity determined by those who use this invention; for example, the cut-off value of the ApoE-rich HDL-C/HDL-C ratio is within the range of 0.0899±20%, and is preferably within the range of 0.0840 to 0.0971, and is most preferably 0.0899.

Figure 9:
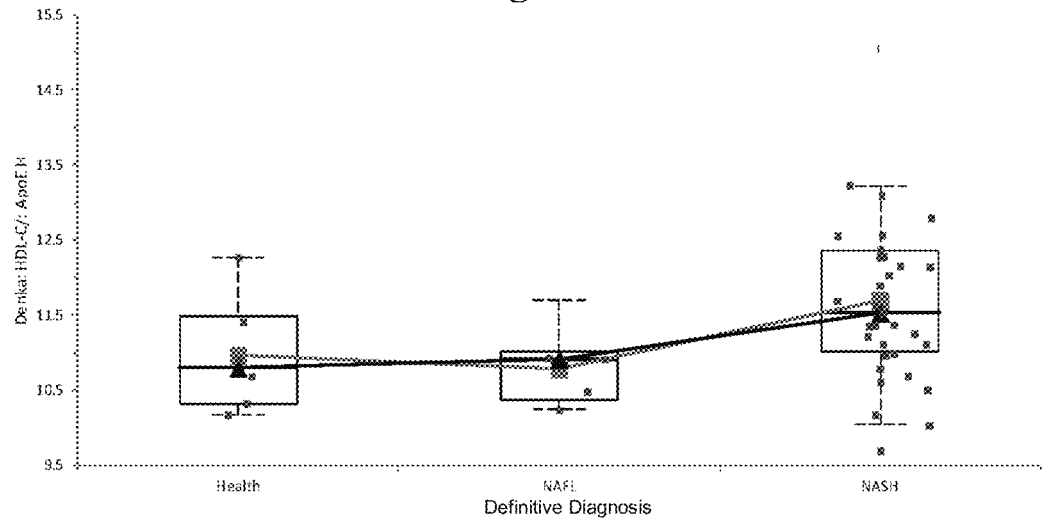
FIG. 9 shows the result of calculating the HDL-C/ApoE-rich HDL-C ratio in blood samples collected from test subjects in Example 3-2.

Furthermore, the HDL-C/ApoE-rich HDL-C ratio in the blood sample is calculated as an index. If the HDL-C/ApoE-rich HDL-C ratio in the blood sample is significantly higher than that in blood samples from healthy individuals or NAFL patients, the HDL-C/ApoE-rich HDL-C ratio in the blood sample can also be recognized as indicating a greater possibility of having NASH (see Example 3-2, Example 13-2, and FIG. 9). The analysis of the HDL-C/ApoE-rich HDL-C ratio in a blood sample identifies a NASH patient with a sensitivity of 80.0% and a specificity of 66.7% when the cut-off value is set at 10.97, and with a sensitivity of 74.3% and a specificity of 88.9% when the cut-off value is set at 11.12, and with a sensitivity of 91.4% and a specificity of 11.1% when the cut-off value is set at 10.30, and with a sensitivity of 42.9% and a specificity of 100% when the cut-off value is set at 11.90. In this case, the HDL-C/ApoE-rich HDL-C ratio is the inverse ratio of the above ApoE-rich HDL-C/HDL-C ratio. In this respect, the cut-off value used to identify NASH patients can be set at an appropriate value within the range depending on the sensitivity and specificity determined by those who use this invention; for example, the cut-off value of the HDL-C/ApoE-rich HDL-C ratio is within the range of 11.12±20%, and is preferably within the range of 10.30 to 11.90, and is most preferably 11.12.

As seen above, the methods of determining the high possibility of having NASH by using, as an index, the abundance of LDL-TG, the LDL-C/LDL-TG ratio, or the ApoE-rich HDL-C/HDL-C ratio in a test blood sample have been described. The detection of NASH may be sufficiently assisted by using any one of those indexes alone, and can be further effectively assisted by using a combination of several of the indexes.

As described above, the abundance of LDL-TG and/or ApoE-rich HDL-C contained in a test blood sample is measured, and the resulting measured values are used as indexes to allow assistance in distinguishing between NASH and NAFL by means of a simple operation, for which liver biopsy has conventionally been required.

(Method of Assisting in Determining the Degree of Progression of Medical Condition Associated with Nonalcoholic Steatohepatitis)

The method of the present invention for assisting in determining the degree of progression of at least one medical condition associated with nonalcoholic steatohepatitis (NASH), which medical condition(s) is(are) selected from the group consisting of fatty degeneration (steatosis), ballooning degeneration, inflammation, and fibrosis, is specifically described below.

(1) Abundance of LDL-TG

The LDL-TG content in a test blood sample is measured as an index. A higher LDL-TG content in the test blood sample can be recognized as indicating a more advanced stage of fatty degeneration (steatosis), inflammation, or ballooning degeneration.

Figure 10:
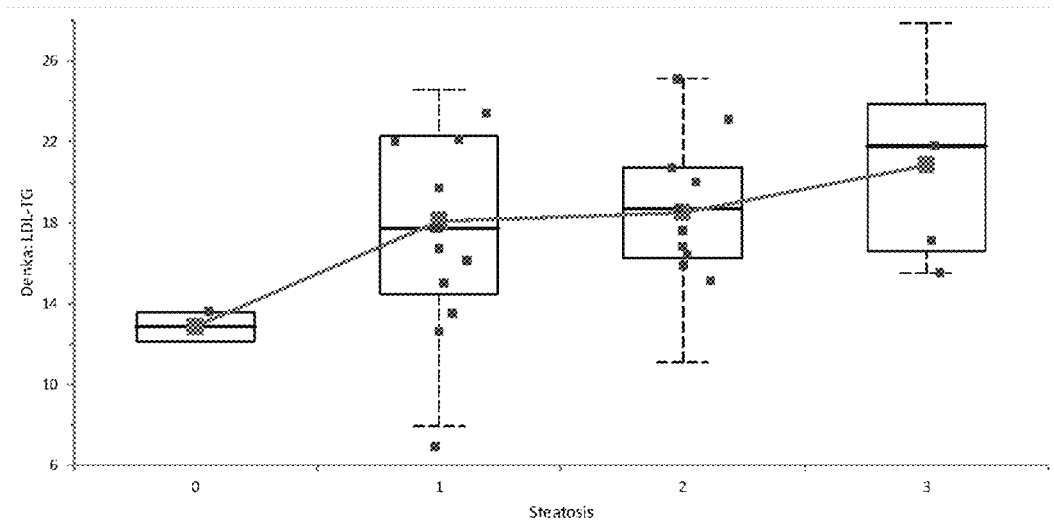
FIG. 10 shows the result of measuring and comparing the LDL-TG contents in blood samples collected from patients with NAFLD according to the stage of fatty degeneration (steatosis) in Example 6-1.

Specifically, an LDL-TG content of not less than 12.2 mg/dL, even not less than 13.7 mg/dL, particularly not less than 14.2 mg/dL, in the test blood sample can be recognized as indicating that fatty degeneration (steatosis) is much more likely to have advanced to Stage 1 or later stages (see Example 6-1 and FIG. 10).

Figure 15:
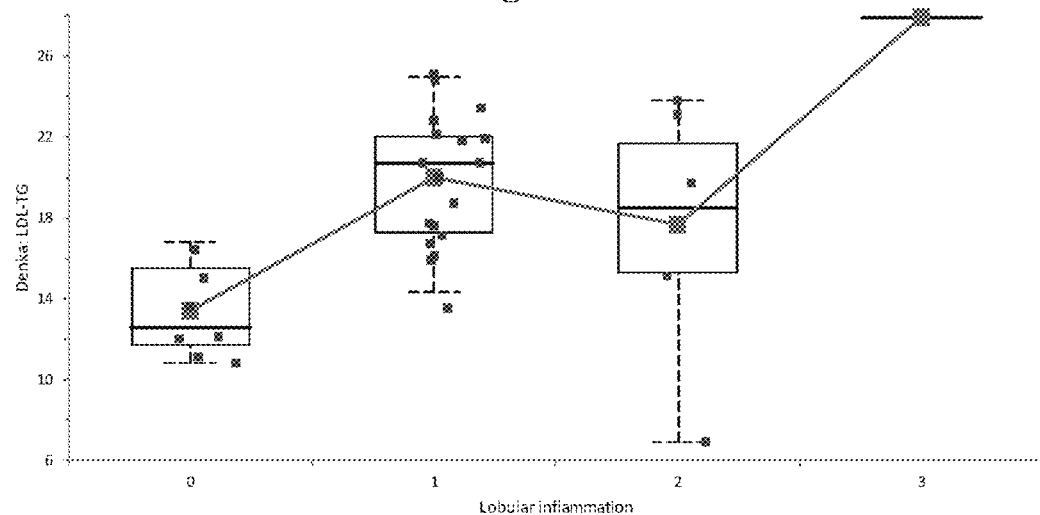
FIG. 15 shows the result of measuring and comparing the LDL-TG contents in blood samples collected from patients with NAFLD according to the stage of inflammation in Example 8.

Additionally, an LDL-TG content of not less than 15.1 mg/dL, even not less than 16.9 mg/dL, in the test blood sample can be recognized as indicating that inflammation has advanced to Stage 1 or later stages, and an LDL-TG content of not less than 22.0 mg/dL, even not less than 22.5 mg/dL, in the test blood sample can be recognized as indicating that inflammation is more likely to have advanced to Stage 3 or later stages (see Example 8 and FIG. 15).

Figure 17:
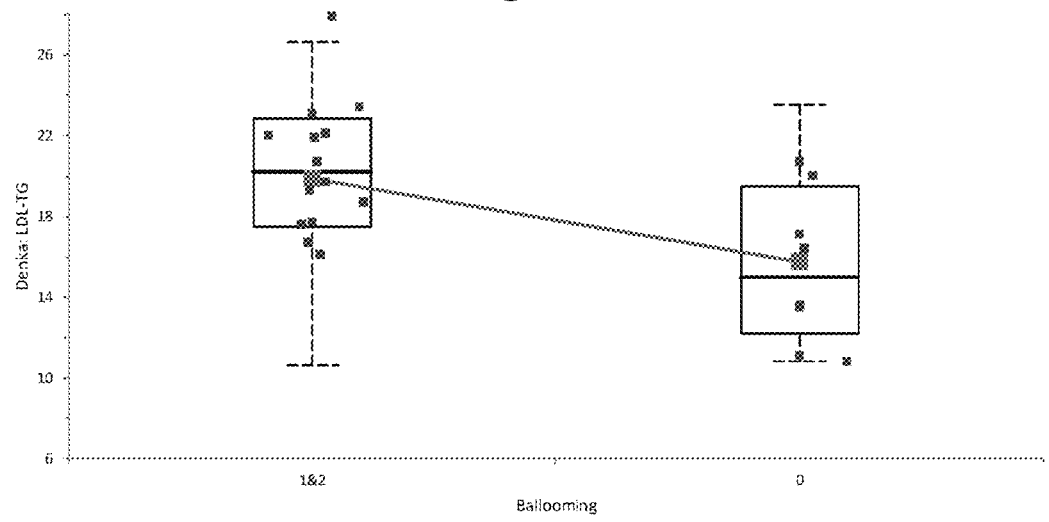
FIG. 17 shows the result of measuring and comparing the LDL-TG contents in blood samples collected from patients with NAFLD according to the stage of ballooning degeneration in Example 10-1.

Additionally, an LDL-TG content of not less than 15.1 mg/dL, even not less than 17.2 mg/dL, particularly not less than 19.5 mg/dL, in the test blood sample can be recognized as indicating that ballooning degeneration is much more likely to have advanced to Stage 1 or later stages (see Example 10-1 and FIG. 17).

(2) LDL-TG/sd LDL-C Ratio

Figure 11:
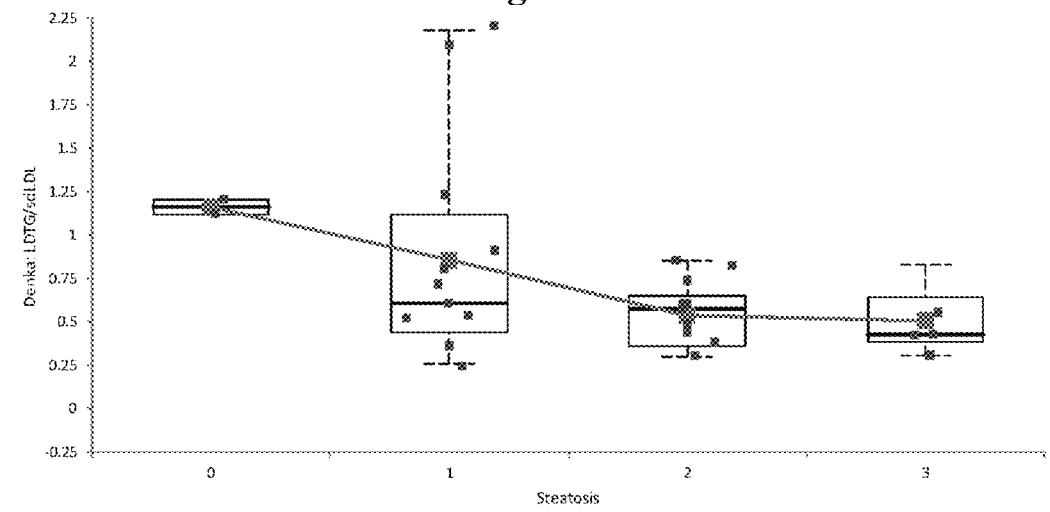
FIG. 11 shows the result of calculating and comparing the LDL-TG/sd LDL-C ratios in blood samples collected from patients with NAFLD according to the stage of fatty degeneration (steatosis) in Example 6-2.

The LDL-TG content and the sd LDL-C content in a test blood sample are measured, and the LDL-TG/sd LDL-C ratio is calculated as an index. A lower LDL-TG/sd LDL-C ratio in the test blood sample can be recognized as indicating a more advanced stage of fatty degeneration (steatosis). In this respect, the sd LDL-C content refers to the abundance of cholesterol (C) in small dense low-density lipoproteins (sd LDL). Specifically, an LDL-TG/sd LDL-C ratio of not more than 1.11, even 0.1 to 1.06, in the test blood sample can be recognized as indicating that fatty degeneration (steatosis) is more likely to have advanced to Stage 1 or later stages (see Example 6-2 and FIG. 11).

Figure 22:
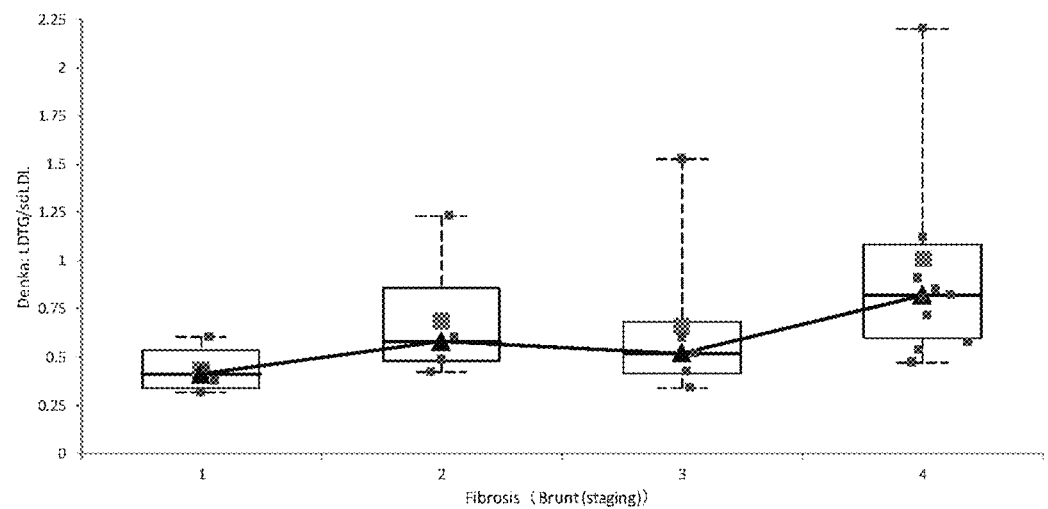
FIG. 22 shows the result of calculating and comparing the LDL-TG/sd LDL-C ratios in blood samples collected from NASH patients according to the stage of fibrosis in Example 11-3.

Additionally, a higher LDL-TG/sd LDL-C ratio in the test blood sample can be recognized as indicating a more advanced stage of fibrosis. Specifically, an LDL-TG/sd LDL-C ratio of not less than 0.39, even not less than 0.60, in the test blood sample can be recognized as indicating that fibrosis is much more likely to have advanced to Stage 2 or later stages, and an LDL-TG/sd LDL-C ratio of not less than 0.61, even not less than 0.72, particularly not less than 0.88, in the test blood sample can be recognized as indicating that fibrosis is more likely to have advanced to Stage 4 or later stages (see Example 11-3 and FIG. 22).

Figure 12:
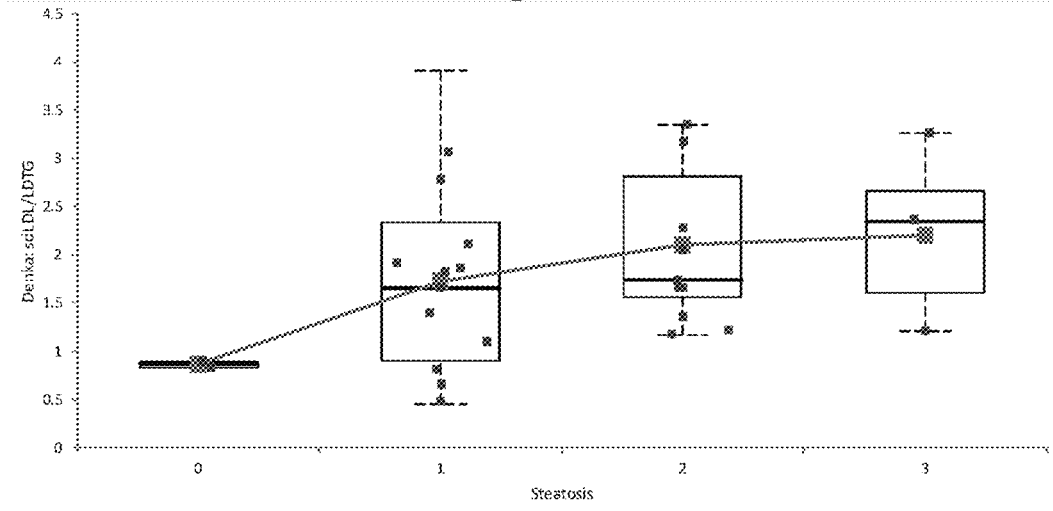
FIG. 12 shows the result of calculating and comparing the sd LDL-C/LDL-TG ratios in blood samples collected from patients with NAFLD according to the stage of fatty degeneration (steatosis) in Example 6-3.
Figure 23:
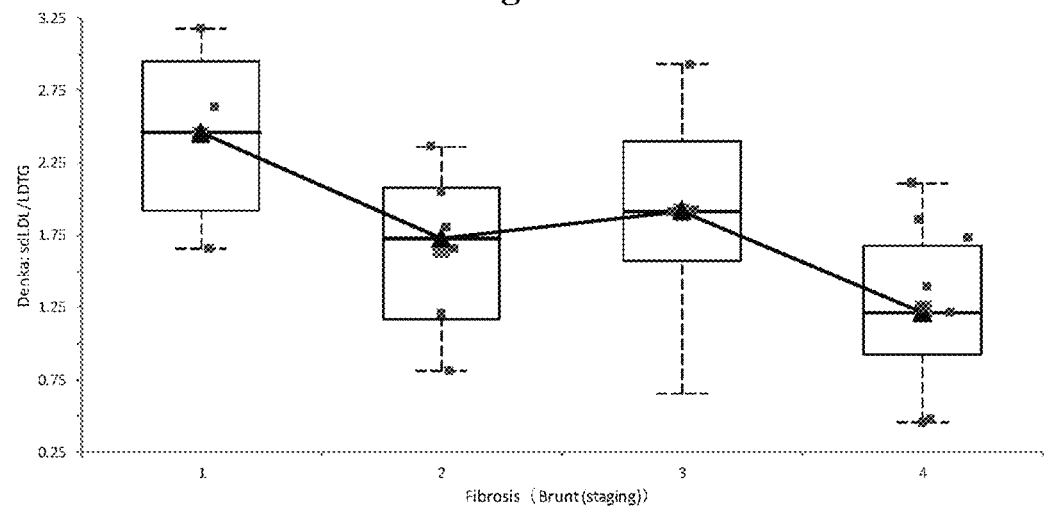
FIG. 23 shows the result of calculating and comparing the sd LDL-C/LDL-TG ratios in blood samples collected from NASH patients according to the stage of fibrosis in Example 11-4.

Furthermore, the sd LDL-C/LDL-TG ratio in a test blood sample can be used as an index to determine the stage of fatty degeneration (steatosis) or fibrosis. In this case, the sd LDL-C/LDL-TG ratio is the inverse ratio of the above LDL-TG/sd LDL-C ratio (FIG. 12, FIG. 23).

(3) ApoE-Rich HDL-C/HDL-C Ratio

Figure 13:
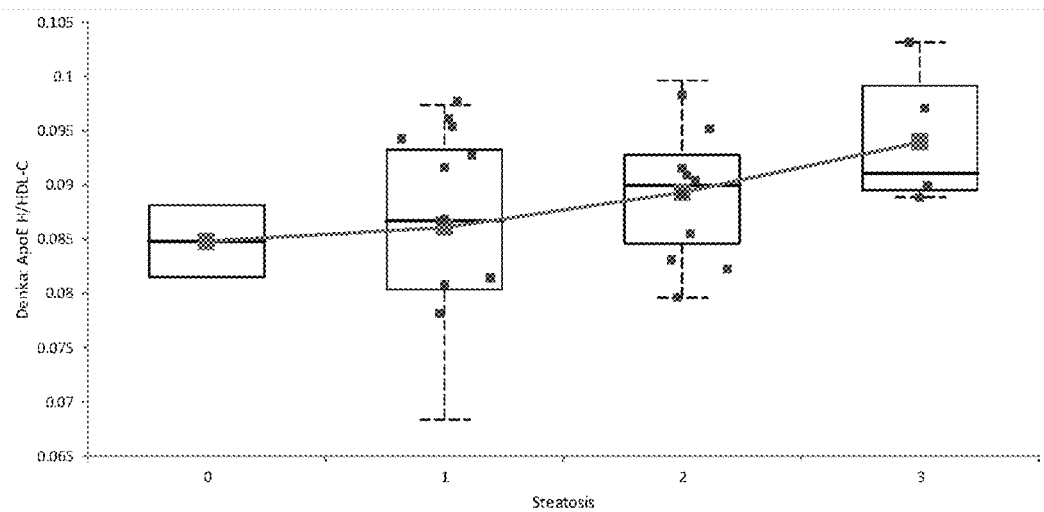
FIG. 13 shows the result of calculating and comparing the ApoE-rich HDL-C/HDL-C ratios in blood samples collected from patients with NAFLD according to the stage of fatty degeneration (steatosis) in Example 7-1.

The ApoE-rich HDL-C content and the HDL-C content in a test blood sample are measured, and the ApoE-rich HDL-C/HDL-C ratio is calculated as an index. A higher ApoE-rich HDL-C/HDL-C ratio in the test blood sample can be recognized as indicating a more advanced stage of fatty degeneration (steatosis). Specifically, an ApoE-rich HDL-C/HDL-C ratio of not less than 0.089, even not less than 0.09, in the test blood sample can be recognized as indicating that fatty degeneration (steatosis) is more likely to have advanced to Stage 1 or later stages (see Example 7-1 and FIG. 13).

Figure 24:
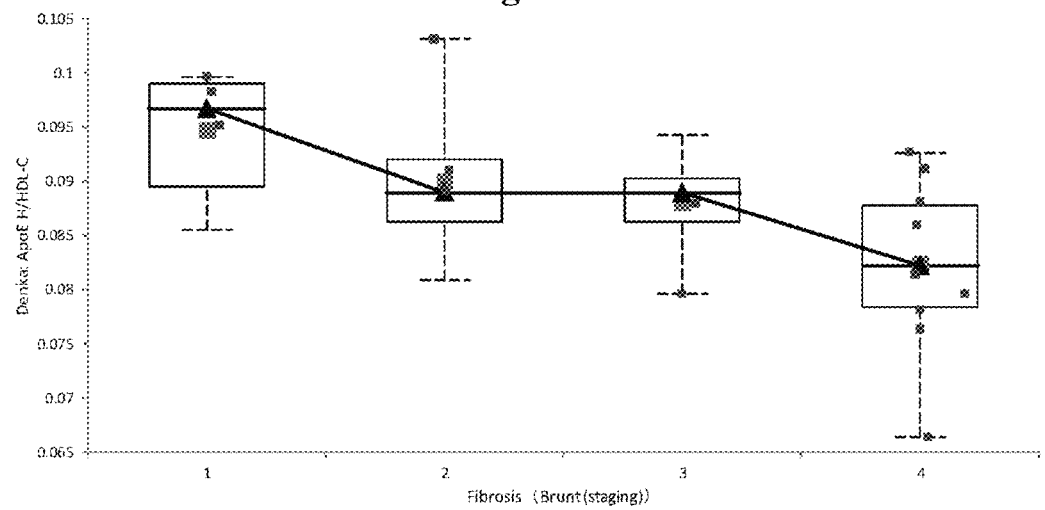
FIG. 24 shows the result of calculating and comparing the ApoE-rich HDL-C/HDL-C ratios in blood samples collected from NASH patients according to the stage of fibrosis in Example 12-1.

Additionally, the ApoE-rich HDL-C/HDL-C ratio in a test blood sample is used as an index, and a lower ApoE-rich HDL-C/HDL-C ratio in the test blood sample can be recognized as indicating a more advanced stage of fibrosis. Specifically, an ApoE-rich HDL-C/HDL-C ratio of not more than 0.095, even not more than 0.094, particularly not more than 0.092, in the test blood sample can be recognized as indicating that fibrosis is more likely to have advanced to Stage 2 or later stages, and an ApoE-rich HDL-C/HDL-C ratio of not more than 0.094, even not more than 0.086, particularly not more than 0.084, in the test blood sample can be recognized as indicating that fibrosis is more likely to have advanced to Stage 4 or later stages (see Example 12-1 and FIG. 24).

Figure 14:
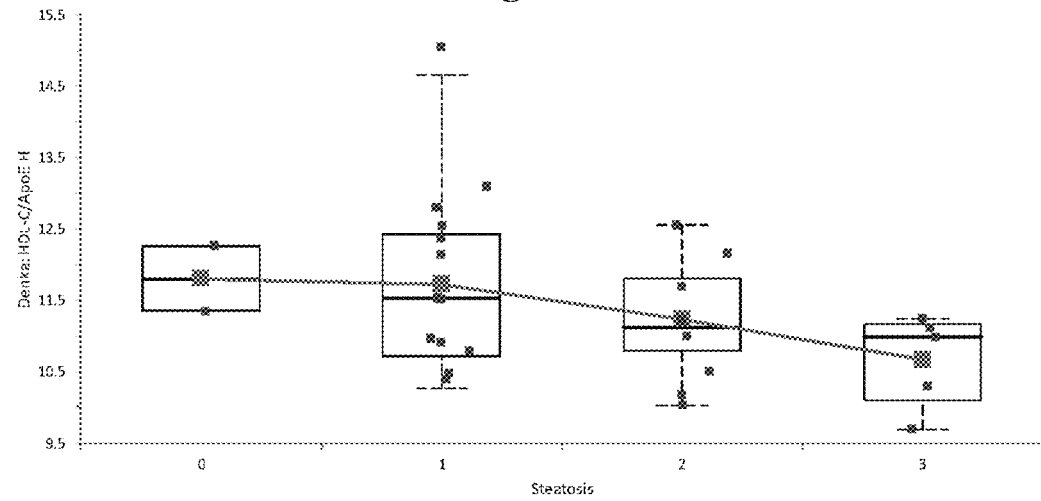
FIG. 14 shows the result of calculating and comparing the HDL-C/ApoE-rich HDL-C ratios in blood samples collected from patients with NAFLD according to the stage of fatty degeneration (steatosis) in Example 7-2.
Figure 25:
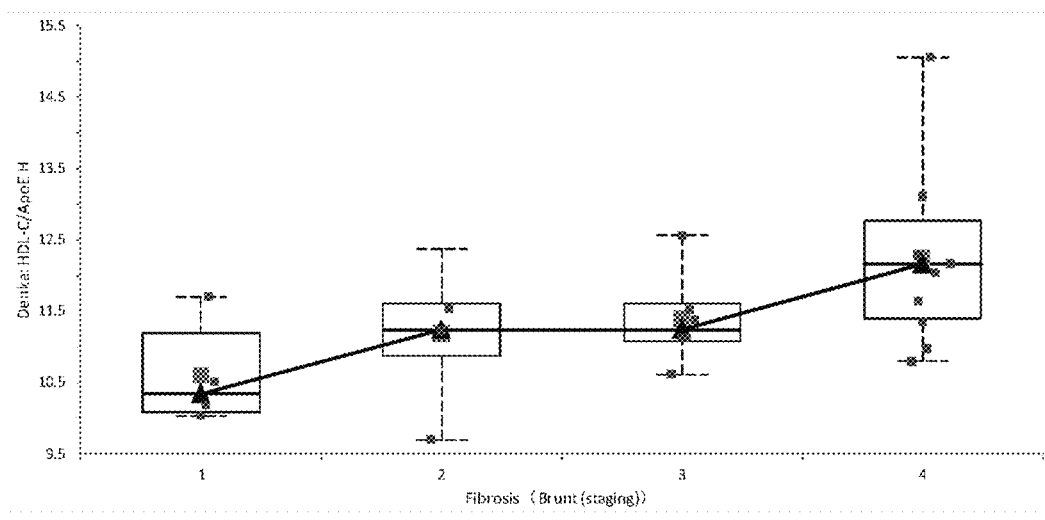
FIG. 25 shows the result of calculating and comparing the HDL-C/ApoE-rich HDL-C ratios in blood samples collected from NASH patients according to the stage of fibrosis in Example 12-2.

Furthermore, the HDL-C/ApoE-rich HDL-C ratio in a test blood sample can be used as an index to determine the stage of fatty degeneration (steatosis) or fibrosis. In this case, the HDL-C/ApoE-rich HDL-C ratio is the inverse ratio of the above ApoE-rich HDL-C/HDL-C ratio (FIG. 14, FIG. 25).

(4) ApoE-Rich HDL-C Content

Figure 16:
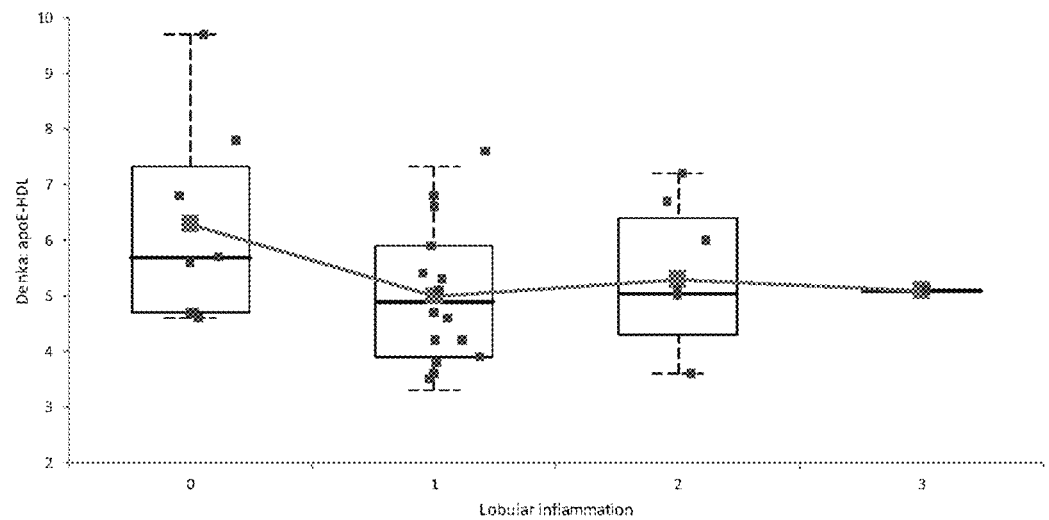
FIG. 16 shows the result of measuring and comparing the ApoE-rich HDL-C contents in blood samples collected from patients with NAFLD according to the stage of inflammation in Example 9.

The ApoE-rich HDL-C content in a test blood sample is measured as an index, and a lower ApoE-rich HDL-C content in the test blood sample can be recognized as indicating a more advanced stage of inflammation. Specifically, an ApoE-rich HDL-C content of not more than 5.5 mg/dL, even not more than 4.6 mg/dL, particularly not more than 4.4 mg/dL, in the test blood sample can be recognized as indicating that inflammation is much more likely to have advanced to Stage 1 or 2 (see Example 9 and FIG. 16).

(5) LDL-TG/LDL-C Ratio

Figure 18:
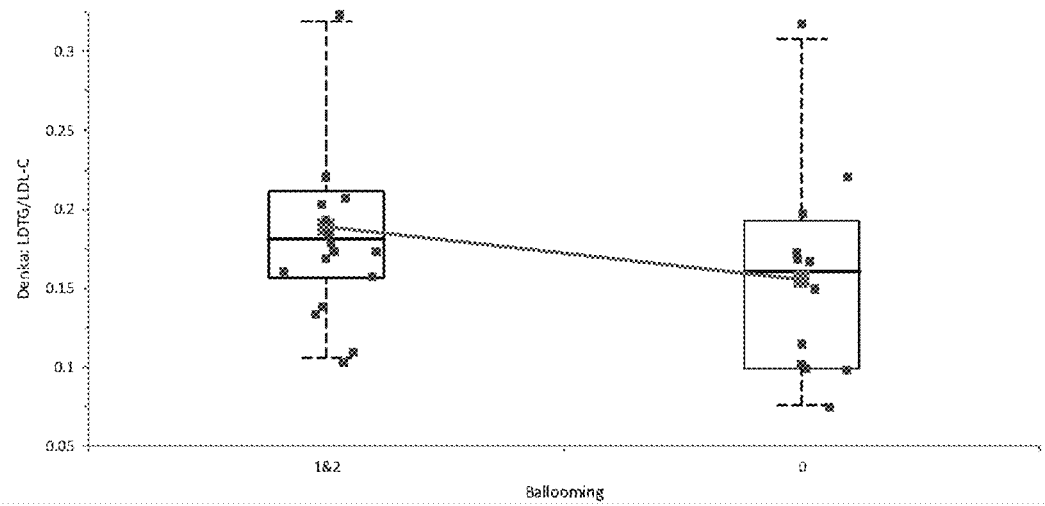
FIG. 18 shows the result of calculating and comparing the LDL-TG/LDL-C ratios in blood samples collected from patients with NAFLD according to the stage of ballooning degeneration in Example 10-2.

The LDL-TG content and the LDL-C content in a test blood sample are measured, and the LDL-TG/LDL-C ratio is calculated as an index. A higher LDL-TG/LDL-C ratio in the test blood sample can be recognized as indicating a more advanced stage of ballooning degeneration. Specifically, an LDL-TG/LDL-C ratio of not less than 0.15, even not less than 0.18, particularly not less than 0.19, in the test blood sample can be recognized as indicating that ballooning degeneration is more likely to have advanced to Stage 1 or later stages (see Example 10-2 and FIG. 18).

Figure 20:
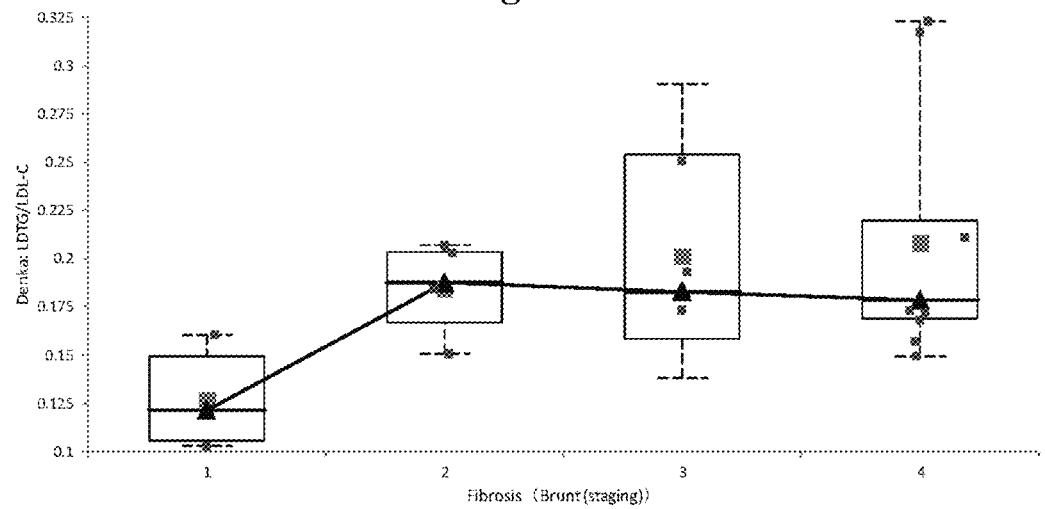
FIG. 20 shows the result of calculating and comparing the LDL-TG/LDL-C ratios in blood samples collected from NASH patients according to the stage of fibrosis in Example 11-1.

Additionally, the LDL-TG/LDL-C ratio in a test blood sample is used as an index, and a higher LDL-TG/LDL-C ratio in the test blood sample can be recognized as indicating a more advanced stage of fibrosis. Specifically, an LDL-TG/LDL-C ratio of not less than 0.14, even not less than 0.17, in the test blood sample can be recognized as indicating that fibrosis is much more likely to have advanced to Stage 2 or later stages (see Example 11-1 and FIG. 20).

Figure 19:
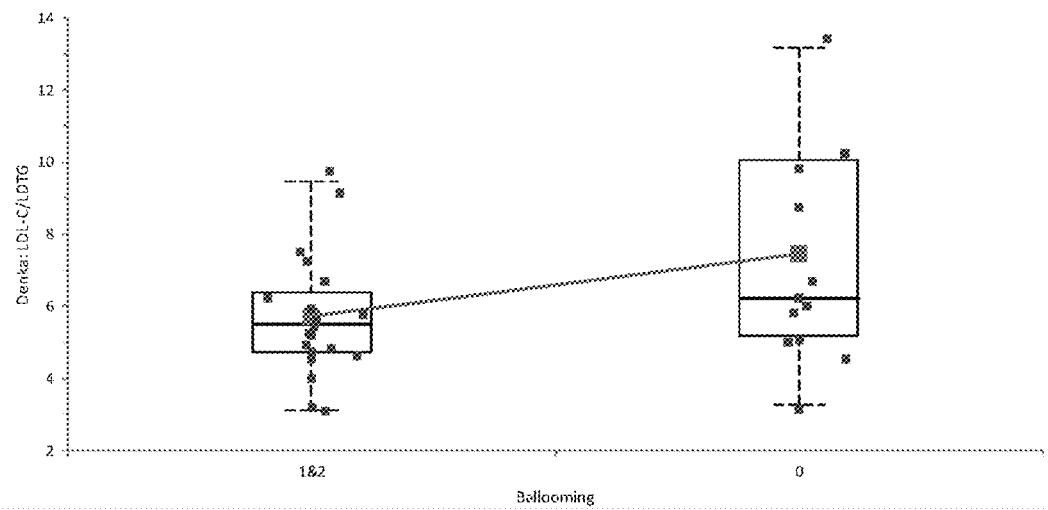
FIG. 19 shows the result of calculating and comparing the LDL-C/LDL-TG ratios in blood samples collected from patients with NAFLD according to the stage of ballooning degeneration in Example 10-3.
Figure 21:
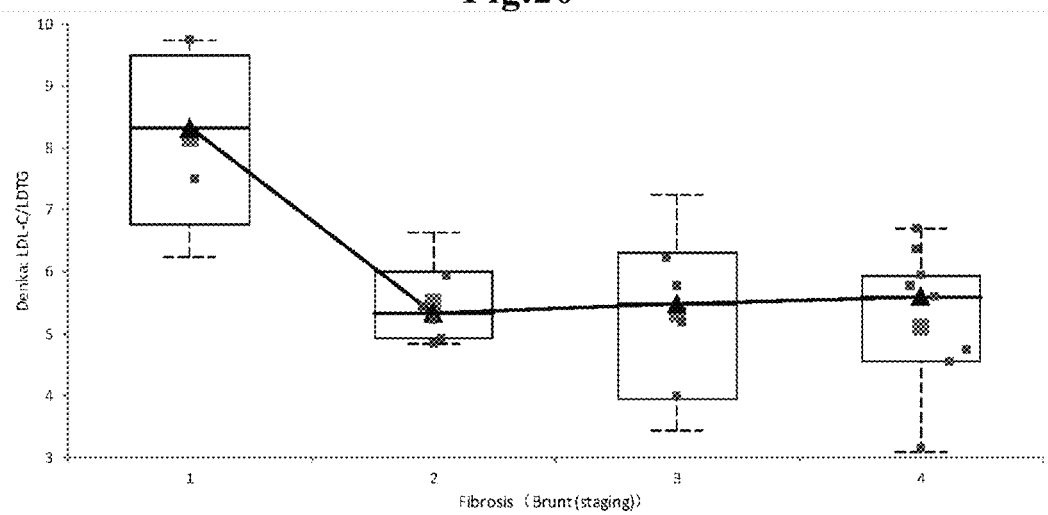
FIG. 21 shows the result of calculating and comparing the LDL-C/LDL-TG ratios in blood samples collected from NASH patients according to the stage of fibrosis in Example 11-2.

Furthermore, the LDL-C/LDL-TG ratio in a test blood sample can be used as an index to determine the stage of ballooning degeneration or fibrosis. In this case, the LDL-C/LDL-TG ratio is the inverse ratio of the above LDL-TG/LDL-C ratio (FIG. 19 and FIG. 21).

As seen above, the methods of assisting in determining the degree of progression of any of the conditions associated with NASH by using, as an index, the abundance of LDL-TG, the LDL-TG/sd LDL-C ratio, the ApoE-rich HDL-C/HDL-C ratio, the ApoE-rich IIDL-C content, or the LDL-TG/LDL-C ratio in a test blood sample have been described. The determination of the degree of progression may be sufficiently assisted by using any one of those indexes alone, and can be further effectively assisted by using a combination of several of the indexes.

As described above, the abundance of LDL-TG and/or ApoE-rich HDL-C contained in a test blood sample is measured, and the resulting measured values are used as indexes to allow assistance in determining the progression stage of any condition associated with NASH by means of a simple operation, for which liver biopsy has conventionally been required.

In the present invention, conventionally known methods can be used as methods of measuring the abundances of LDL-TG, ApoE-rich HDL-C, HDL-C, LDL-C, and sd LDL-C contained in blood samples. Examples of the methods include a method in which the amount of triglycerides or cholesterol is measured by any quantitative procedure following separation of lipoproteins of interest by a fractionation procedure such as ultracentrifugation, electrophoresis, or high performance liquid chromatography, and a method in which triglycerides and cholesterol in all lipoproteins but lipoproteins of interest are removed in the first step without fractionation, followed by measurement of triglycerides or cholesterol in the lipoproteins of interest in the second step.

Specifically, the method described in WO 2013/157642 can be used as a method of measuring the LDL-TG content, and the method described in WO 98/26090 can be used as a method of measuring the HDL-C content, and the method described in WO 98/47005 can be used as a method of measuring the LDL-C content, and the method described in WO 2009/048143 can be used as a method of measuring the sd LDL-C content.

EXAMPLES

The present invention is specifically described below by way of examples, but the present invention is not limited to the following examples.

Comparative Example 1

Figure 1:
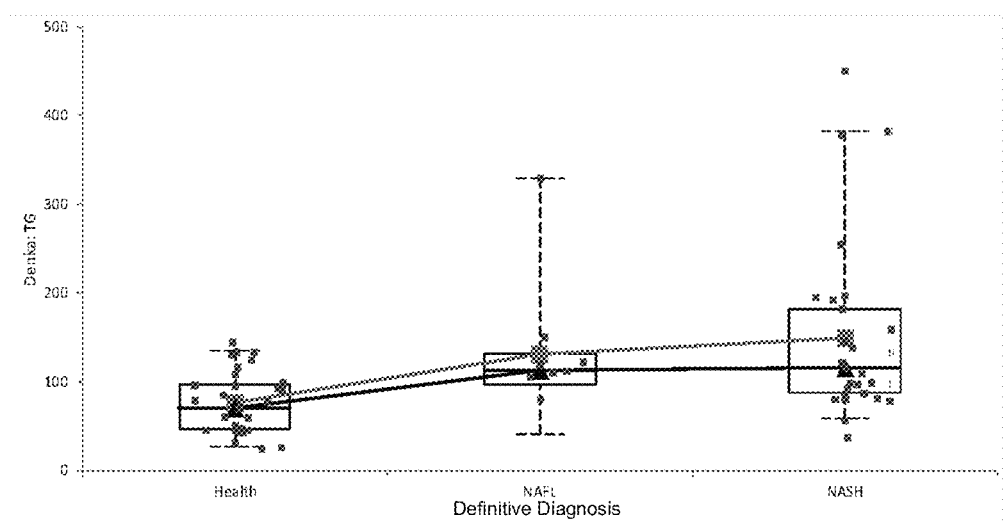
FIG. 1 shows the result of measuring the total TG content in blood samples collected from test subjects in Comparative Example 1.

The total TG content was measured in blood samples collected from a total of 80 subjects in a population, which was composed of 36 healthy individuals (denoted by "Health" in the drawings), 9 NAFT, patients, and 35 NASH patients, and was compared between groups. An automated analyzer used in medical laboratories was used to measure the total TG content by means of a triglyceride assay reagent TG-EX "SEIKEN" (an enzymatic assay) (manufactured by Denka SEIKEN Co., Ltd.). The comparison is graphically represented in FIG. 1.

The result indicated that the total TG content of the NASH group was significantly higher compared to that of the group of healthy individuals ($p<0.0001$) but was not significantly different from that of the NAFL, group, and that the total TG content of the NAFL group was significantly higher compared to that of the group of healthy individuals ($p<0.05$).

Comparative Example 2

Figure 2:
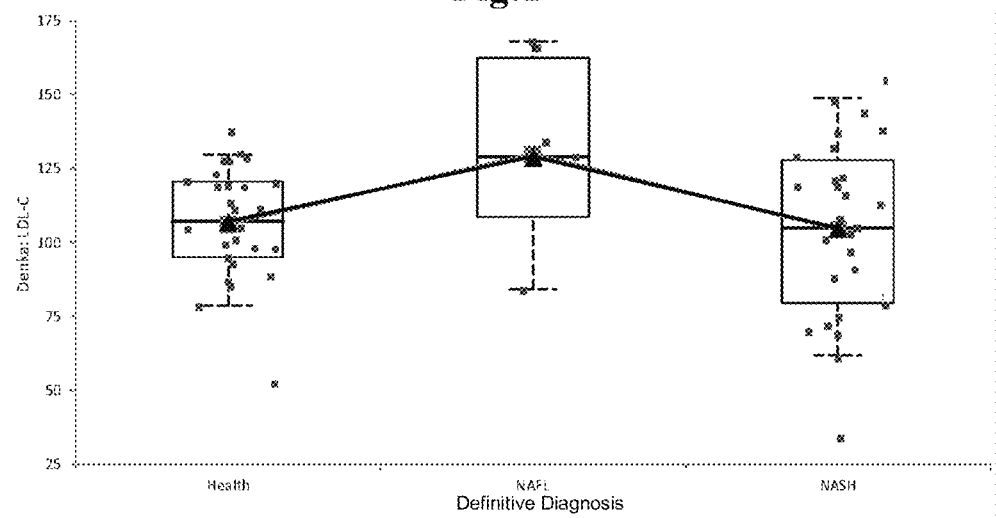
FIG. 2 shows the result of measuring the LDL-C content in blood samples collected from test subjects in Comparative Example 2.

The LDL-C content was measured in the blood samples collected from a total of 80 subjects in the same population as in Comparative Example 1, which was composed of 36 healthy individuals (Health), 9 NAFL patients, and 35 NASH patients, and was compared between groups. An automated analyzer used in medical laboratories was used to measure the LDL-C content by means of an LDL-cholesterol assay reagent for automated analysis "SEIKEN" LDL-EX(N) (a direct assay) (manufactured by Denka SEIKEN Co., Ltd.). The comparison is graphically represented in FIG. 2.

The result indicated that the LDL-C content of the NASH group tended to be lower compared to that of the NAFL group but was not significantly different from that of the group of healthy individuals, and that, moreover, the LDL-C content of the NAFL group tended to be higher compared to that of the group of healthy individuals.

Comparative Example 3

Figure 3:
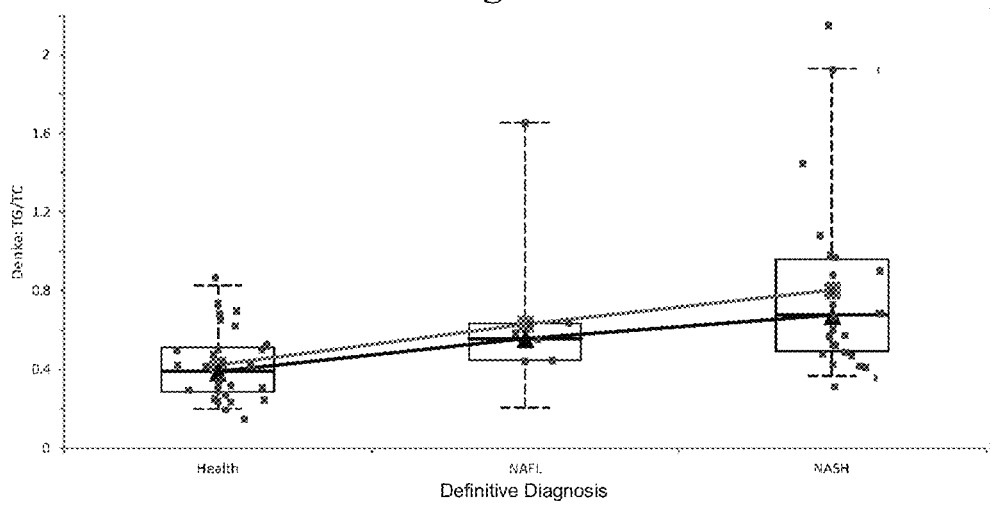
FIG. 3 shows the result of calculating the total TG/TC ratio in blood samples collected from test subjects in Comparative Example 3.

The total cholesterol (TC) content and the total TG content were measured in the blood samples collected from a total of 80 subjects in the same population as in Comparative Example 1, which was composed of 36 healthy individuals (Health), 9 NAFL patients and 35 NASH patients, to calculate the total TG/TC ratio in each group, and the resulting ratio was compared between groups. The total TG content was measured by the same method as in Comparative Example 1, and an automated analyzer used in medical laboratories was used to measure the TC content by means of a cholesterol assay reagent for automated analysis "SEIKEN" T-CHO(S) (an enzymatic assay) (manufactured by Denka SEIKEN Co., Ltd.). The comparison is graphically represented in FIG. 3.

The result indicated that the total TG/TC ratio of the NASH group was significantly higher compared to that of the group of healthy individuals ($p<0.0001$) but was not significantly different compared to that of the NAFL group, and that, moreover, the total TG/TC ratio of the NAFL group was not significantly different compared to that of the group of healthy individuals.

Example 1

The LDL-TG content was measured in the blood samples collected from a total of 80 subjects in the same population as in Comparative Example 1, which was composed of 36 healthy individuals (Health), 9 NAFL patients, and 35 NASH patients, and was compared between groups. An automated analyzer used in medical laboratories was used to measure the LDL-TG content by means of an LDL-triglyceride assay reagent LDL TG-EX "SEIKEN" (manufactured by Denka SEIKEN Co., Ltd.). The comparison is graphically represented in FIG. 4.

The result indicated that the LDL-TG content of the NASH group was significantly higher compared to that of the NAFL group ($p<0.05$) and that of the group of healthy individuals ($p<0.0001$), and that, moreover, the LDL-TG content of the NAFL group was significantly higher than that of the group of healthy individuals ($p<0.05$).

Example 2-1

The LDL-TG content and the LDL-C content were measured in the blood samples collected from a total of 80 subjects in the same population as in Comparative Example 1, which was composed of 36 healthy individuals (Health), 9 NAFL patients, and 35 NASH patients, by the same methods as in Example 1 and Comparative Example 2 to calculate the LDL-TG/LDL-C ratio in each group, and the resulting ratio was compared between groups. The comparison is graphically represented in FIG. 5.

The result indicated that the LDL-TG/LDL-C ratio of the NASH group was significantly higher compared to that of the NAFL group ($p<0.05$) and was also significantly higher compared to that of the group of healthy individuals (p<0.0001), and that, moreover, the LDL-TG/LDL-C ratio was not significantly different between the NAFL group and the group of healthy individuals.

Example 2-2

The LDL-TG content and the LDL-C content were measured in the blood samples collected from a total of 80 subjects in the same population as in Comparative Example 1, which was composed of 36 healthy individuals (Health), 9 NAFL patients, and 35 NASH patients, by the same methods as in Example 1 and Comparative Example 2 to calculate the LDL-C/LDL-TG in each group, and the resulting ratio was compared between groups. The comparison is graphically represented in FIG. 6.

The result indicated that the LDL-C/LDL-TG ratio of the NASH group was significantly lower compared to that of the NAFL group (p<0.05) and was also significantly lower compared to that of the group of healthy individuals (p<0.0001), and that, moreover, the LDL-C/LDL-TG ratio was not significantly different between the NAFL group and the group of healthy individuals.

As demonstrated in <Comparative Example 1>, <Comparative Example 2>, and <Comparative Example 3>, the NASH and NAFL groups failed to be clearly distinguished by measuring total TG content, LDL-C content, or TC content. However, as demonstrated in <Example 1> of the present invention, the three groups of NASH, NAFL, and healthy individuals were able to be clearly distinguished by measuring LDL-TG content. Additionally, as demonstrated in <Example 2-1> and <Example 2-2> of the present invention, the NASH and NAFL groups were further able to be clearly distinguished by calculating the ratio between LDL-TG and LDL-C.

Comparative Example 4

Figure 7:
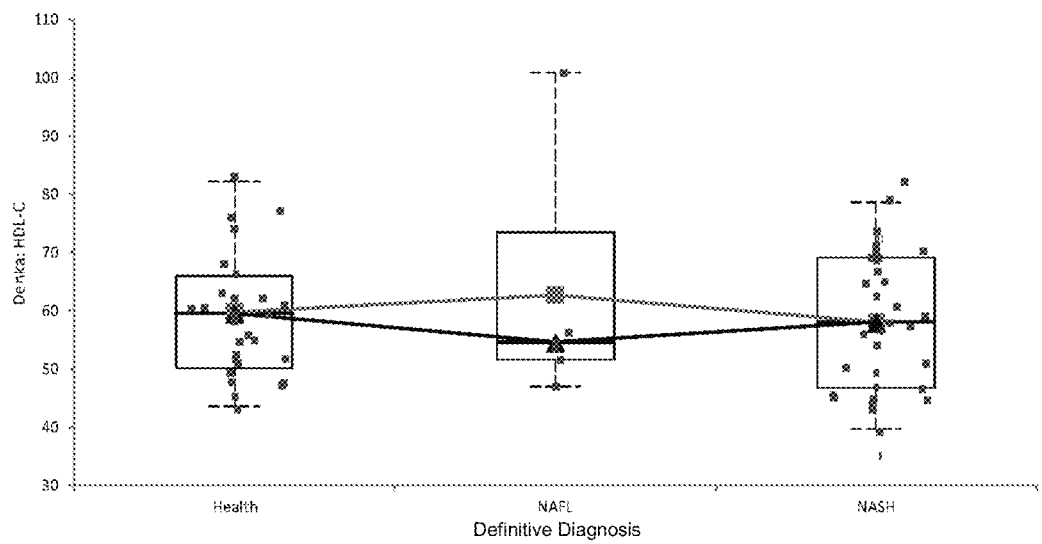
FIG. 7 shows the result of measuring the HDL-C content in blood samples collected from test subjects in Comparative Example 4.

The HDL-C content was measured in the blood samples collected from a total of 80 subjects in the same population as in Comparative Example 1, which was composed of 36 healthy individuals (Health), 9 NAFL patients, and 35 NASH patients, and was compared between groups. An automated analyzer was used to measure the HDL-C content by means of an HDL-cholesterol assay reagent for automated analysis "SEIKEN" HDL-EX (a direct assay) (manufactured by Denka SEIKEN Co., Ltd.). The comparison is graphically represented in FIG. 7.

The result indicated that the HDL-C content was not significantly different between the three groups of NASH, NAFL, and healthy individuals.

Example 3-1

The ApoE-rich HDL-C and the HDL-C content were measured in blood samples collected from a total of 50 subjects in a population, which was composed of 6 healthy individuals (Health), 9 NAFL patients, and 35 NASH patients, to calculate the ApoE-rich HDL/HDL-C ratio in each group, and the resulting ratio was compared between groups. An automated analyzer used in medical laboratories was used to measure the ApoE-rich HDL-C content by means of an ApoE-rich HDL-cholesterol assay reagent, and the HDL-C content was measured by the same method as in Comparative Example 4. The ApoE-rich HDL-cholesterol assay reagent was used according to the method described in JP 2014-030393 A. The comparison is graphically represented in FIG. 8.

The result indicated that the ApoE-rich HDL-C/HDL-C ratio of the NASH group was significantly lower compared to that of the NAFL group (p<0.05), and that, moreover, the ApoE-rich HDL-C/HDL-C ratio was not significantly different between the NAFL group and the group of healthy individuals.

Example 3-2

The ApoF-rich HDL-C content and the HDL-C content were measured in the blood samples collected from a total of 50 subjects in the population, which was composed of 6 healthy individuals (Health), 9 NAFL patients, and 35 NASH patients, by the same methods as in Example 3-1 and Comparative Example 4 to calculate the HDL-C/ApoE-rich HDL-C ratio in each group, and the resulting ratio was compared between groups. The comparison is graphically represented in FIG. 9.

The result indicated that the HDL-C/ApoE-rich HDL-C ratio of the NASH group was significantly higher compared to that of the NAFL group (p<0.05), and that, moreover, the HDL-C/ApoE-rich HDL-C ratio was not significantly different between the NAFL group and the group of healthy individuals.

As demonstrated in <Comparative Example 4>, the NASH and NAFL groups failed to be distinguished by comparing only the HDL-C contents. However, as demonstrated in <Example 3-1> and <Example 3-2>, the NASH and NAFL groups were able to be clearly distinguished by calculating the ratio between ApoE-rich HDL-C and HDL-C.

Example 4

The LDL-TG content was measured in blood samples collected from a total of 44 subjects in an NAFLD population, which was composed of 9 NAFL, patients and 35 NASH patients, to perform ROC analysis, and the AUC was found to be 0.78 (95% CI: 0.63-0.92), which was a satisfactory result.

In this population, the sensitivity and specificity were 82.9% and 55.6%, respectively, when the cut-off value was set at 15.1 mg/dL, and were 65.7% and 88.9%, respectively, when the cut-off value was set at 17.6 mg/dL. Furthermore, the sensitivity and specificity were 94.3% and 22.2%, respectively, when the cut-off value was set at 12.1 mg/dL, and were 48.6% and 100%, respectively, when the cut-off value was set at 20.2 mg/dL.

Example 5-1

The blood LDL-C content was measured in the same population as in Example 4, and the LDL-TG/LDL-C ratio was calculated to perform ROC analysis, and the AUC was found to be 0.86 (95% CI: 0.70-1.02), which was a satisfactory result.

In this population, the sensitivity and specificity of LDL-TG/LDL-C ratio were 100% and 55.6%, respectively, when the cut-off value was set at 0.13, and were 94.3% and 66.7%, respectively, when the cut-off value was set at 0.133. Furthermore, the sensitivity and specificity were 82.9% and 77.8%, respectively, when the cut-off value was set at 0.149, and were 31.4% and 100%, respectively, when the cut-off value was set at 0.203.

Example 5-2

The LDL-C/LDL-TG ratio was calculated from the blood LDL-TG content and the blood LDL-C content in the same population as in Example 5-1 to perform ROC analysis, and the AUC was found to be 0.86 (95% CI:0.70-1.02), which was a satisfactory result.

In this population, the sensitivity and specificity of LDL-C/LDL-TG ratio were 100% and 55.6%, respectively, when the cut-off value was set at 9.75, and were 94.3% and 66.7%, respectively, when the cut-off value was set at 7.50. Furthermore, the sensitivity and specificity were 82.9% and 77.8%, respectively, when the cut-off value was set at 6.70 and were 31.4% and 100%, respectively, when the cut-off value was set at 4.93.

Example 6-1

The LDL-TG content was measured in blood samples collected from patients with NAFLD (n=37), in which the stage of fatty degeneration (steatosis) had been identified in each patient, by the same method as in Example 1, and was compared between stage groups. The comparison is graphically represented in FIG. 10.

The result indicated that the LDL-TG content was significantly higher in the Stage 1, Stage 2, and Stage 3 groups than in the Stage 0 group ($p<0.05$, $p<0.05$, and $p<0.05$, respectively). Moreover, the mean in each stage group was found to be 12.2 mg/dL, 18.1 mg/dL, 18.5 mg/dL, and 20.8 mg/dL in the Stage 0, Stage 1, Stage 2, and Stage 3 groups, respectively.

Example 6-2

The LDL-TG content and the sd LDL-C content were measured in the blood samples collected from patients with NAFLD (n=37), in which the stage of fatty degeneration (steatosis) had been identified in each patient, to calculate the ratio between them, and the resulting ratio was compared between stage groups. The LDL-TG content was measured by the same method as in Example 1, and an automated analyzer was used to measure the sd LDL-C content by means of a sd LDL-cholesterol assay reagent sd LDL-EX "SEIKEN" (manufactured by Denka SEIKEN Co., Ltd.). The comparison is graphically represented in FIG. 11.

The result indicated that the LDL-TG/sd LDL-C ratio was significantly lower in the Stage 2 group than in the Stage 0 group ($p<0.05$), and tended to be lower in the Stage 3 group than in the Stage 0 group. Moreover, the median in each stage group was found to be 1.120, 0.604, 0.576, and 0.426 in the Stage 0, Stage 1, Stage 2, and Stage 3 groups, respectively.

Example 6-3

The LDL-TG content and the sd LDL-C content were measured in the blood samples collected from patients with NAFLD (n=37), in which the stage of fatty degeneration (steatosis) had been identified in each patient, by the same methods as in Example 1 and Example 6-2 to calculate the ratio between them, and the resulting ratio was compared between stage groups. The comparison is graphically represented in FIG. 12.

The result indicated that the sd LDL-C/LDL-TG ratio was significantly higher in the Stage 2 group than in the Stage 0 group ($p<0.05$), and tended to be higher in the Stage 3 group than in the Stage 0 group. Moreover, the median in each stage group was found to be 0.893, 1.655, 1.735, and 2.349 in the Stage 0, Stage 1, Stage 2, and Stage 3 groups, respectively.

As demonstrated in <Example 6-1> to <Example 6-3> of the present invention, the progression stage of fatty degeneration (steatosis) can be deduced by analyzing the LDL-TG content or the ratio between LDL-TG and sd LDL-C.

Example 7-1

The ApoE-rich HDL-C content and the HDL-C content were measured in the blood samples collected from patients with NAFLD (n=37), in which the stage of fatty degeneration (steatosis) had been identified in each patient, by the same methods as in Example 3-1 and Comparative Example 4 to calculate the ratio between them, and the resulting ratio was compared between stage groups. The comparison is graphically represented in FIG. 13.

The result indicated that the ApoE-rich HDL-C/HDL-C ratio was significantly higher in the Stage 3 group than in the Stage 1 group ($p<0.05$).

Example 7-2

The ApoE-rich HDL-C content and the HDL-C content were measured in the blood samples collected from patients with NAFLD (n=37), in which the stage of fatty degeneration (steatosis) had been identified in each patient, by the same methods as in Example 3-1 and Comparative Example 4 to calculate the ratio between them, and the resulting ratio was compared between stage groups. The comparison is graphically represented in FIG. 14.

The result indicated that the HDL-C/ApoE-rich HDL-C ratio tended to be lower in the Stage 3 group than in the Stage 0 group.

As demonstrated in <Example 7-1> and <Example 7-2> of the present invention, the progression stage of fatty degeneration (steatosis) can be deduced by analyzing the ratio between ApoE-rich HDL-C and HDL-C.

Example 8

The LDL-TG content was measured in blood samples collected from patients with NAFLD (n=38), in which the stage of inflammation had been identified in each patient, by the same method as in Example 1, and was compared between stages. The comparison is graphically represented in FIG. 15.

The result indicated that LDL-TG content was significantly higher in the Stage 3 group than in the Stage 0, Stage 1, and Stage 2 groups ($p<0.001$, $p<0.05$, and $p<0.05$, respectively), and was significantly higher in the Stage 2 group than in the Stage 0 group ($p<0.05$), and was significantly higher in the Stage 1 group than in the Stage 0 group ($p<0.0001$).

Example 9

The ApoE-rich HDL-C content was measured in the blood samples collected from patients with NAFLD (n=38), in which the stage of inflammation had been identified in each patient, by the same method as in Example 3-1, and was compared between stages. The comparison is graphically represented in FIG. 16.

The result indicated that ApoE-rich HDL-C content was significantly lower in the Stage 1 group than in the Stage 0 group ($p<0.05$).

As demonstrated in <Example 8> and <Example 9> of the present invention, the progression stage of inflammation can be deduced by analyzing the LDL-TG content or the ApoE-rich HDL-C content.

Example 10-1

The LDL-TG content was measured in blood samples collected from patients with NAFLD (n=37), in which the stage of ballooning degeneration (Ballooning) had been identified in each patient, by the same method as in Example 1, and was compared between stages. The comparison is graphically represented in FIG. 17.

The result indicated that LDL-TG content was significantly higher in the combined group of Stages 1 and 2 than in the Stage 0 group ($p<0.01$).

Example 10-2

The LDL-TG content and the LDL-C content were measured in the blood samples collected from patients with NAFLD (n=37), in which the stage of ballooning degeneration (Ballooning) had been identified in each patient, by the same methods as in Example 1 and Comparative Example 2 to calculate the ratio between them, and the resulting ratio was compared between stages. The comparison is graphically represented in FIG. 18.

The result indicated that the LDL-TG/LDL-C ratio tended to be higher in the combined group of Stages 1 and 2 than in the Stage 0 group.

Example 10-3

The LDL-TG content and the LDL-C content were measured in the blood samples collected from patients with NAFLD (n=37), in which the stage of ballooning degeneration (Ballooning) had been identified in each patient, by the same methods as in Example 1 and Comparative Example 2 to calculate the ratio between them, and the resulting ratio was compared between stages. The comparison is graphically represented in FIG. 19.

The result indicated that the LDL-C/LDL-TG ratio was significantly lower in the combined group of Stages 1 and 2 than in the Stage 0 group ($p<0.05$).

As demonstrated in <Example 10-1>, <Example 10-2>, and <Example 10-3> of the present invention, the progression stage of ballooning degeneration (Ballooning) can be deduced by analyzing the LDL-TG content or the ratio between LDL-TG and LDL-C.

Example 11-1

The LDL-TG content and the LDL-C content were measured in blood samples collected from NASH patients (n=27), in which the stage of fibrosis had been identified in each patient, by the same methods as in Example 1 and Comparative Example 2 to calculate the ratio between them, and the resulting ratio was compared between stage groups. The comparison is graphically represented in FIG. 20.

The result indicated that the LDL-TG/LDL-C ratio was significantly higher in the Stage 2, Stage 3, and Stage 4 groups than in the Stage 1 group ($p<0.05$, $p<0.05$, and $p<0.01$, respectively).

Example 11-2

The LDL-TG content and the LDL-C content were measured in the blood samples collected from NASH patients (n=27), in which the stage of fibrosis had been identified in each patient, by the same methods as in Example 1 and Comparative Example 2 to calculate the ratio between them, and the resulting ratio was compared between stage groups. The comparison is graphically represented in FIG. 21.

The result indicated that the LDL-C/LDL-TG ratio was significantly lower in the Stage 2, Stage 3, and Stage 4 groups than in the Stage 1 group ($p<0.005$, $p<0.005$, and $p<0.0005$, respectively).

Example 11-3

The LDL-TG content and the sd LDL-C content were measured in the blood samples collected from NASH patients (n=27), in which the stage of fibrosis had been identified in each patient, by the same methods as in Example 1 and Example 6-2 to calculate the ratio between them, and the resulting ratio was compared between stage groups. The comparison is graphically represented in FIG. 22.

The result indicated that the LDL-TG/sd LDL-C ratio was significantly higher in the Stage 4 group than in the Stage 1 group ($p<0.05$), and tended to be higher in the Stage 4 group than in the Stage 3 group, and also tended to be higher in the Stage 2 group than in the Stage 1 group.

Example 11-4

The LDL-TG content and the sd LDL-C content were measured in the blood samples collected from NASH patients (n=27), in which the stage of fibrosis had been identified in each patient, by the same methods as in Example 1 and Example 6-2 to calculate the ratio between them, and the resulting ratio was compared between stage groups. The comparison is graphically represented in FIG. 23.

The result indicated that the sd LDL-C/LDL-TG ratio was significantly lower in the Stage 4 group than in the Stage 1 and Stage 3 groups ($p<0.005$ and $p<0.05$, respectively), and also tended to be lower in the Stage 2 group than in the Stage 1 group.

As demonstrated in <Examples 11-1 to -4> of the present invention, the progression stage of fibrosis can be deduced by analyzing the ratio between LDL-TG and LDL-C or the ratio between LDL-TG and sd LDL-C.

Example 12-1

The ApoE-rich HDL-C content and the HDL-C content were measured in the blood samples collected from NASH patients (n=27), in which the stage of fibrosis had been identified in each patient, by the same methods as in Example 3-1 and Comparative Example 4 to calculate the ratio between them, and the resulting ratio was compared between stage groups. The comparison is graphically represented in FIG. 24.

The ApoE-rich HDL-C/HDL-C ratio was significantly lower in the Stage 4 group than in the Stage 1 and Stage 2 groups ($p<0.005$ and $p<0.05$, respectively).

Example 12-2

The ApoE-rich HDL-C content and the HDL-C content were measured in the blood samples collected from NASH patients (n=27), in which the stage of fibrosis had been identified in each patient, by the same methods as in Example 3-1 and Comparative Example 4 to calculate the ratio between them, and the resulting ratio was compared between stage groups. The comparison is graphically represented in FIG. 25.

The HDL-C/ApoE-rich HDL-C ratio was significantly higher in the Stage 4 group than in the Stage 1 and Stage 2 groups ($p<0.01$ and $p<0.05$, respectively), and tended to be higher in the Stage 4 group than in the Stage 3 group.

As demonstrated in <Example 12-1> and <Example 12-2> of the present invention, the progression stage of fibrosis can be deduced by analyzing the ratio between ApoE-rich HDL-C and HDL-C.

Example 13-1

The blood ApoE-rich HDL-C content and the blood HDL-C content were measured in the same population as in Example 4, and the ApoE-rich HDL-C/HDL-C ratio was calculated to perform ROC analysis, and the AUC was found to be 0.80 (95% CI: 0.65-0.94), which was a satisfactory result.

In this population, the sensitivity and specificity of the ApoE-rich HDL-C/HDL-C ratio were 80.0% and 66.7%, respectively, when the cut-off value was set at 0.0912, and were 74.3% and 88.9%, respectively, when the cut-off value was set at 0.0899. Furthermore, the sensitivity and specificity were 42.9% and 100%, respectively, when the cut-off value was set at 0.0840, and were 91.4% and 11.1%, respectively, when the cut-off value was set at 0.0971.

Example 13-2

The HDL-C/ApoE-rich HDL-C ratio was calculated from the blood ApoE-rich HDL-C content and the blood HDL-C content in the same population as in Example 13-1 to perform ROC analysis, and the AUC was found to be 0.80 (95% CI: 0.65-0.94), which was a satisfactory result.

In this population, the sensitivity and specificity of the HDL-C/ApoE-rich HDL-C ratio were 80.0% and 66.7%, respectively, when the cut-off value was set at 10.97, and were 74.3% and 88.9%, respectively, when the cut-off value was set at 11.12. Furthermore, the sensitivity and specificity were 91.4% and 11.1%, respectively, when the cut-off value was set at 10.30, and were 42.9% and 100%, respectively, when the cut-off value was set at 11.90.

The invention claimed is:

1. A method of detecting low-density lipoprotein-triglyceride (LDL-TG) in a test blood sample isolated from a living body of a patient having nonalcoholic fatty liver disease, said method comprising detecting whether LDL-TG is present at a concentration of 12.1 mg/dL or more in the sample.

2. A method of detecting low-density lipoprotein-triglyceride (LDL-TG) and LDL-C in a test blood sample isolated from a living body of a patient having nonalcoholic fatty liver disease, said method comprising:
    measuring the abundance of LDL-TG and LDL-C in the sample;
    calculating LDL-TG/LDL-C ratio in the sample; and
    detecting whether LDL-TG and LDL-C are present at a LDL-TG/LDLC ratio of 0.103 or more in the sample.

3. A method of detecting apolipoprotein E-rich high-density lipoprotein-cholesterol (ApoE-rich HDL-C) and HDL-C in a test blood sample isolated from a living body of a patient having nonalcoholic fatty liver disease, said method comprising:
    measuring the abundance of ApoE-rich HDL-C and HDL-C in the sample;
    calculating ApoE-rich HDL-C/HDL-C ratio in the sample; and
    detecting whether ApoE-rich HDL-C and HDL-C are present at a ApoE-rich HDL-C/HDL-C ratio of 0.089 or more in the sample.

4. A method of detecting apolipoprotein E-rich high-density lipoprotein-cholesterol (ApoE-rich HDL-C) in a test blood sample isolated from a living body of a patient having nonalcoholic fatty liver disease, said method comprising detecting whether ApoE-rich HDL-C is present at a concentration of 5.5 mg/dL or less in the sample.

5. A method of detecting apolipoprotein E-rich high density lipoprotein-cholesterol (ApoE-rich HDL-C) and HDL-C in a test blood sample isolated from a living body of a patient having nonalcoholic fatty liver disease, said method comprising:
    measuring the abundance of ApoE-rich HDL-C and HDL-C in the sample;
    calculating ApoE-rich HDL-C/HDL-C ratio in the sample; and
    detecting whether ApoE-rich HDL-C and HDL-C are present at a ApoE-rich HDL-C/HDL-C ratio of 0.0971 or less in the sample.

6. The method of detecting low-density lipoprotein-triglyceride (LDL-TG), according to claim 1, wherein whether LDL-TG is present at a concentration of 17.6 mg/dL or more in the sample is detected.

7. The method of detecting low-density lipoprotein-triglyceride (LDL-TG) and LDL-C, according to claim 2, wherein whether LDL-TG and LDL-C are present at a LDL-TG/LDL-C ratio of 0.133 or more in the sample is detected.

8. The method of detecting apolipoprotein E-rich high-density lipoprotein-cholesterol (ApoE-rich HDL-C) and HDL-C, according to claim 3, wherein whether ApoE-rich HDL-C and HDL-C are present at a ApoE-rich HDL-C/HDL-C ratio between 0.089 and 0.0971 in the sample is detected.

9. The method of detecting apolipoprotein E-rich high-density lipoprotein-cholesterol (ApoE-rich HDL-C), according to claim 4, wherein whether ApoE-rich HDL-C is present at a concentration of 4.4 mg/dL or less in the sample.

10. The method of detecting apolipoprotein E-rich high-density lipoprotein-cholesterol (ApoE-rich HDL-C) and HDL-C), according to claim 5, wherein whether ApoE-rich HDL-C and HDL-C are present at a ApoE-rich HDL-C/HDL-C ratio of 0.0899 or less in the sample is detected.

* * * * *